(12) United States Patent
Niwa (10) Patent No.: US 8,521,552 B2
(45) Date of Patent: Aug. 27, 2013

(54) SYSTEM AND METHOD FOR PROVIDING A MEDICAL DEVICE TO A PATIENT

(75) Inventor: Masakazu Niwa, Tokyo (JP)

(73) Assignee: CooperVision International Holding Company, LP, St. Michael (BB)

( * ) Notice: Subject to any disclaimer, the term of this patent is extended or adjusted under 35 U.S.C. 154(b) by 1933 days.

(21) Appl. No.: 11/593,025

(22) Filed: Nov. 6, 2006

(65) Prior Publication Data

US 2008/0004912 A1 Jan. 3, 2008

Related U.S. Application Data

(60) Provisional application No. 60/817,355, filed on Jun. 30, 2006.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC .......................................................... 705/2–3
See application file for complete search history.

(56) References Cited

U.S. PATENT DOCUMENTS

| | | | |
|---|---|---|---|
| 4,958,280 A | 9/1990 | Pauly et al. | |
| 5,620,087 A | 4/1997 | Martin et al. | |
| 5,697,495 A | 12/1997 | Abrams et al. | |
| 5,737,539 A | 4/1998 | Edelson et al. | |
| 6,055,507 A | 4/2000 | Cunningham | |
| 6,315,410 B1 | 11/2001 | Doshi | |
| 6,746,120 B2 | 6/2004 | Broderick et al. | |
| 7,698,156 B2 | 4/2010 | Martucci et al. | |
| 2002/0026768 A1 | 3/2002 | Duncan et al. | |
| 2002/0103673 A1 | 8/2002 | Atwood | |
| 2002/0117405 A1 | 8/2002 | Wang et al. | |
| 2003/0009354 A1* | 1/2003 | Arbogast et al. ................... 705/2 |
| 2004/0004633 A1 | 1/2004 | Perry et al. | |
| 2004/0121767 A1 | 6/2004 | Simpson et al. | |
| 2004/0167465 A1 | 8/2004 | Mihai et al. | |
| 2005/0004700 A1 | 1/2005 | Dimaggio | |
| 2005/0060196 A1 | 3/2005 | Tsushi et al. | |
| 2006/0003906 A1 | 1/2006 | Ohno et al. | |

FOREIGN PATENT DOCUMENTS

| | | |
|---|---|---|
| JP | 11-242699 | 9/1999 |
| JP | 2002-170008 | 6/2002 |
| JP | 2002-258222 | 9/2002 |
| JP | 2003-228623 | 8/2003 |
| JP | 2004-246843 | 9/2004 |
| JP | 2005-327310 | 11/2005 |
| JP | 2006-155618 | 6/2006 |
| WO | WO 85/02700 | 6/1985 |

OTHER PUBLICATIONS

U.S. Appl. No. 09/494,589, Beaton, et al.

* cited by examiner

*Primary Examiner* — Lena Najarian
*Assistant Examiner* — Minnah Seoh
(74) *Attorney, Agent, or Firm* — Steptoe & Johnson LLP (57) ABSTRACT

A computer-implemented system and method for providing a medical device to a patient, including recording, by medical personnel, information specific to a patient; automatically selecting a portion of the recorded patient information; transmitting the selected portion of the recorded patient information to a provider of the medical device; automatically selecting the medical device based on the transmitted patient information; transmitting information describing the selected medical device from the provider of the medical device to the medical personnel; and providing the selected medical device to the patient.

20 Claims, 4 Drawing Sheets

SYSTEM AND METHOD FOR PROVIDING A MEDICAL DEVICE TO A PATIENT

CROSS-REFERENCE TO RELATED APPLICATION

This application is based upon and claims priority from U.S. provisional patent application No. 60/817,355, filed Jun. 30, 2006, the contents of which being incorporated herein by reference.

BACKGROUND

Prior to the specialized division of the provision of health care services and devices, the prescribing and the providing of vision medical devices, including eye glasses and contact lenses, rested with the eye doctor, or optometrist. A patient would be examined by the doctor, who would determine whether the patient needed glasses (or contact lenses); and, if so, would determine not only the correction of the eye lenses needed but also the source from which the eye glasses would be procured. The doctor's office would order the prescribed eye glasses; and, upon the receipt of the glasses at the doctor's office, the patient would be called back to the office, and the glasses would be fitted to the patient. Any subsequent correction or modification of the glasses, frames, and/or prescription would be ordered by the doctor or his/her office from the supplier of the glasses.

Similar methods were followed with other medical devices to be provided to a patient. For example, foot orthotics would be prescribed and ordered by the doctor, to be subsequently fitted to the patient's shoes and feet upon a return visit to the doctor's office. Hearing devices, joint braces, and prostheses are other examples of medical devices that have been provided to a patient under the sole discretion of a medical care and/or device provider.

SUMMARY

Exemplary embodiments are directed to a computer-implemented system and method for providing a medical device to a patient, including recording, by medical personnel, information specific to a patient; automatically determining medical device parameters and selecting a provider of a medical device for the patient; automatically selecting a portion of the recorded patient information; transmitting the selected portion of the recorded patient information to the selected medical device provider; transmitting medical device order information to the selected medical device provider; automatically selecting the medical device based on the transmitted patient and order information; transmitting medical device selection information to the medical personnel; and providing the selected medical device to the patient.

Alternative embodiments provide a computer-based system for providing a medical device to a patient, including a medical computer recording information specific to a patient and recording results of an examination of the patient; a processor on the medical computer selecting a portion of the recorded patient information and a portion of the recorded examination results, wherein at least part of the selected portions are determined based on a medical device to be provided to the patient; a communications device transmitting the selected portions of the recorded patient information and the recorded examination results to a provider of the medical device; a provider computer receiving the transmitted selected portions of the patient information and the examination results; and a processor on the provider computer selecting the medical device for the patient based on the transmitted patient information and examination results and providing notification that the selected medical device is to be delivered to the patient.

An additional embodiment is also directed to a computer-readable medium encoded with computer-executable instructions, which, when executed by a computer, provide for the delivery of a medical device to a patient, wherein the instructions are provided for recording, by medical personnel, patient information; examining the patient for application of a medical device; recording the results of the patient examination; automatically selecting a portion of the recorded patient information and a portion of the recorded examination results, wherein the portions of information to be selected are determined based on the medical device to be provided to the patient; transmitting the selected portions of the recorded patient information and the recorded examination results to a provider of the medical device; automatically selecting the medical device based on the transmitted patient information and examination results; transmitting information describing the selected medical device to the medical personnel; and providing notification that the selected medical device is to be delivered to the patient.

A further embodiment is directed to a computer-based method for providing a medical device to a patient, including triggering a medical device reorder request to a provider of a medical device; determining whether the reorder request for the medical device has been authorized, by medical personnel, for the patient; transmitting, if the reorder is not authorized, a request for approval of the reorder to the medical personnel; receiving, from the medical personnel, a response to the request for approval of the reorder request; and if the response authorizes the reorder request, processing the steps of selecting the medical device to be delivered based on patient and medical device information on file with the provider of the medical device and based on the reorder authorization; transmitting information describing the selected medical device to be reordered to the medical personnel; and providing the selected medical device to the patient.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 1 shows a component diagram of a computer-based system for providing a medical device to a patient.

FIG. 2 shows a block flow chart of an exemplary method for providing a medical device to a patient.

FIG. 3 shows an exemplary block chart of information flowing between a patient, medical personnel, and a medical device provider according to exemplary embodiments.

FIG. 4 shows a block flow chart of an exemplary method for providing a reordered medical device to a patient.

DETAILED DESCRIPTION OF THE EMBODIMENTS

Referring initially to FIG. 1, there is illustrated a computer-based system for providing a medical device to a patient. While exemplary embodiments are described below for providing contact lenses to a patient, the system and method of the invention are not so limited. Embodiments of the invention can be easily extended by persons of skill in the art, in conjunction with the present description of the invention, to the providing of many medical devices to one or more patients, said medical devices including, without limitation, hearing devices, joint braces, orthodics, prostheses, and the like.

Figure 1:
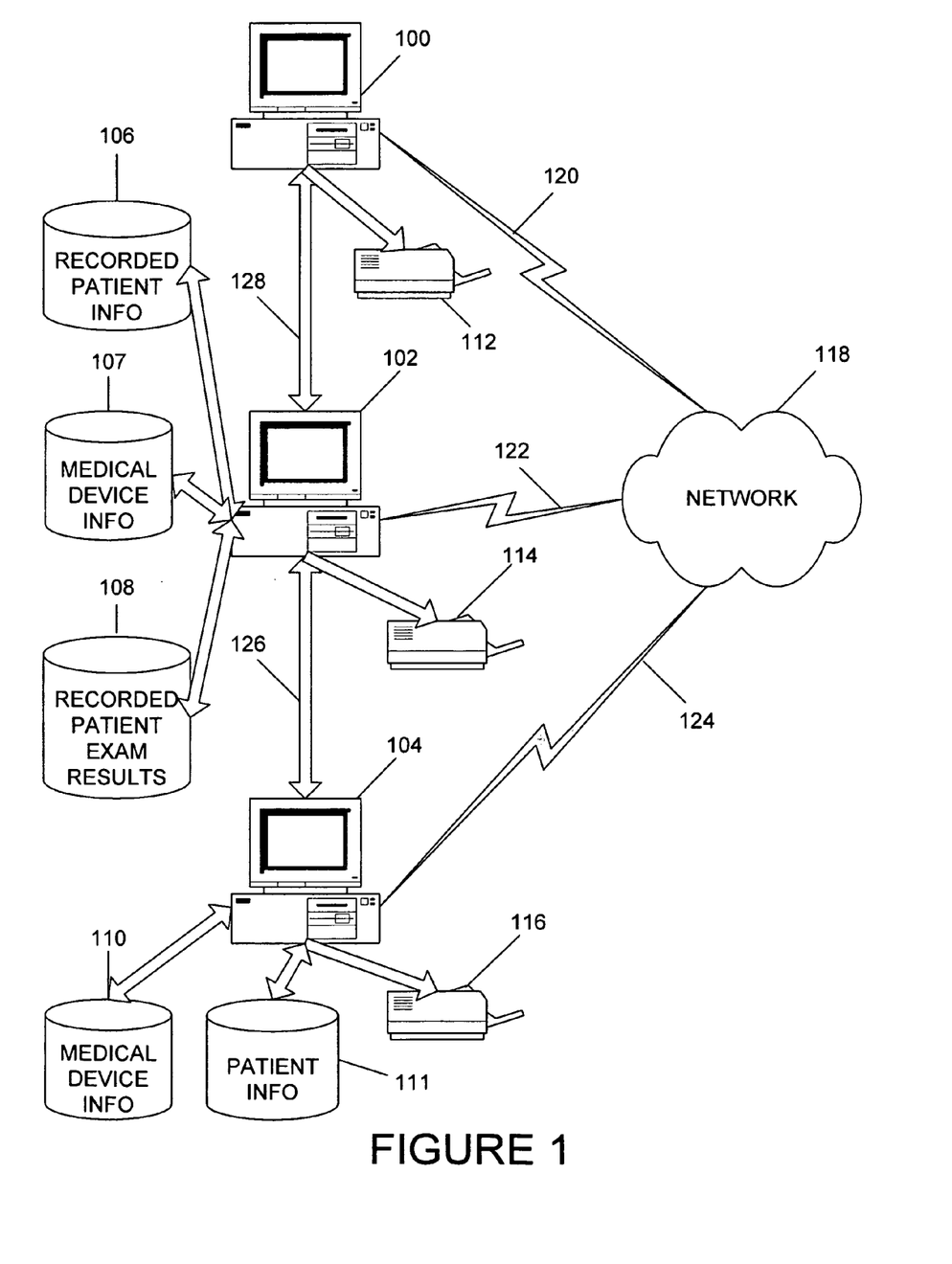

These and other aspects of the medical device providing system and method will now be described in greater detail in connection with a number of exemplary embodiments. To facilitate an understanding of the embodiments, many aspects are described in terms of sequences of actions to be performed by elements of a computer system or apparatus as shown in FIG. 1. It will be recognized that in each of the embodiments, the various actions could be performed by specialized circuits, by computer program or computer product instructions being executed by one or more processors, or by a combination of both. Moreover, embodiments can additionally be considered to be embodied entirely within any form of computer readable storage medium having stored therein an appropriate set of computer instructions that would cause a processor to carry out the techniques, methods, and steps described herein.

FIG. 1 shows a patient computer 100, a medical personnel's computer 102, and a medical device provider's computer 104 connected across a network 118, such as the Internet or an intranet. Each of the computers 100, 102, and 104 have one or more processors for the processing of software instructions, for processing input information, for analyzing information, for automatically making decisions, and for creating output information. Under one or more exemplary embodiments, the patient's computer 100 is not required because information can be sent to the patient optionally electronically and otherwise manually, such as by mail. However, doctor computer 102 and medical device provider computer 104 are utilized in exemplary embodiments and are intended to be separate and distinct computers so as to secure patient information recorded on the medical personnel's computer 102 and storage devices 106 and 108 from the medical device provider's computer 104. In an exemplary embodiment, patient information is not centrally stored in a single computer. Further, as discussed below, only a portion of a patient's information is stored on the medical device provider's computer 104 and/or storage device 111.

The exemplary computers 100, 102, and 104 are not limited to traditional desk-top computers or laptop computers. Processing, communicating, and data transmitting and receiving functions can be implemented in a number of electronic devices within embodiments covered by the present concepts. For example and not limitation, one or more of the exemplary computers can comprise cellular telephones and/or personal digital assistants, including blackberry-type devices.

Computer-executable instructions, or software, are provided for directing the processing of the computers 100, 102, and 104, including processing the steps of exemplary embodiments of the medical device providing system. The computer-executable instructions, when executed by the computers 100, 102, and/or 104 and/or the processors associated with each of said computers, provide for the automatic selection and delivery of one or more medical devices to a patient. One or more disk drives 106, 108, and/or 110 are provided for storage of information utilized in the selection and delivery of the medical devices. The software can be stored on the disk drives, can be loaded into the memory of the computers, or can be stored onto separate storage means within the computers. Further, the software can comprise separate programs and sets of instructions or can be combined into a single program, set of instructions, or program module.

Means for supporting a computer-based system for automatic providing of a medical device to a patient include the computers 100, 102, and/or 104 and their respective processors and storage devices 106, 107, 108, 110, and 111, along with the software, or computer instructions, for directing the computers and/or processors to process patient and medical device information and to select the medical device for the patient based on the patient and medical device information.

The functionality of an embodiment for automatically providing a medical device to a patient can be shown with the following exemplary flow description:

Providing a Medical Device to a Patient:
   Record information specific to a patient
   Examine the patient for application of a medical device
   Record the results of the patient examination
   Automatically select a portion of the recorded patient information
   Automatically select a portion of the recorded examination results
     Wherein the portions of information to be selected are determined based on the medical device to be provided to the patient
   Transmit the selected portions of the recorded patient information and the recorded examination results to a provider of the medical device
   Automatically select the medical device based on the transmitted patient information and examination results
   Provide notification that the selected medical device is to be delivered to the patient.

Figure 2:
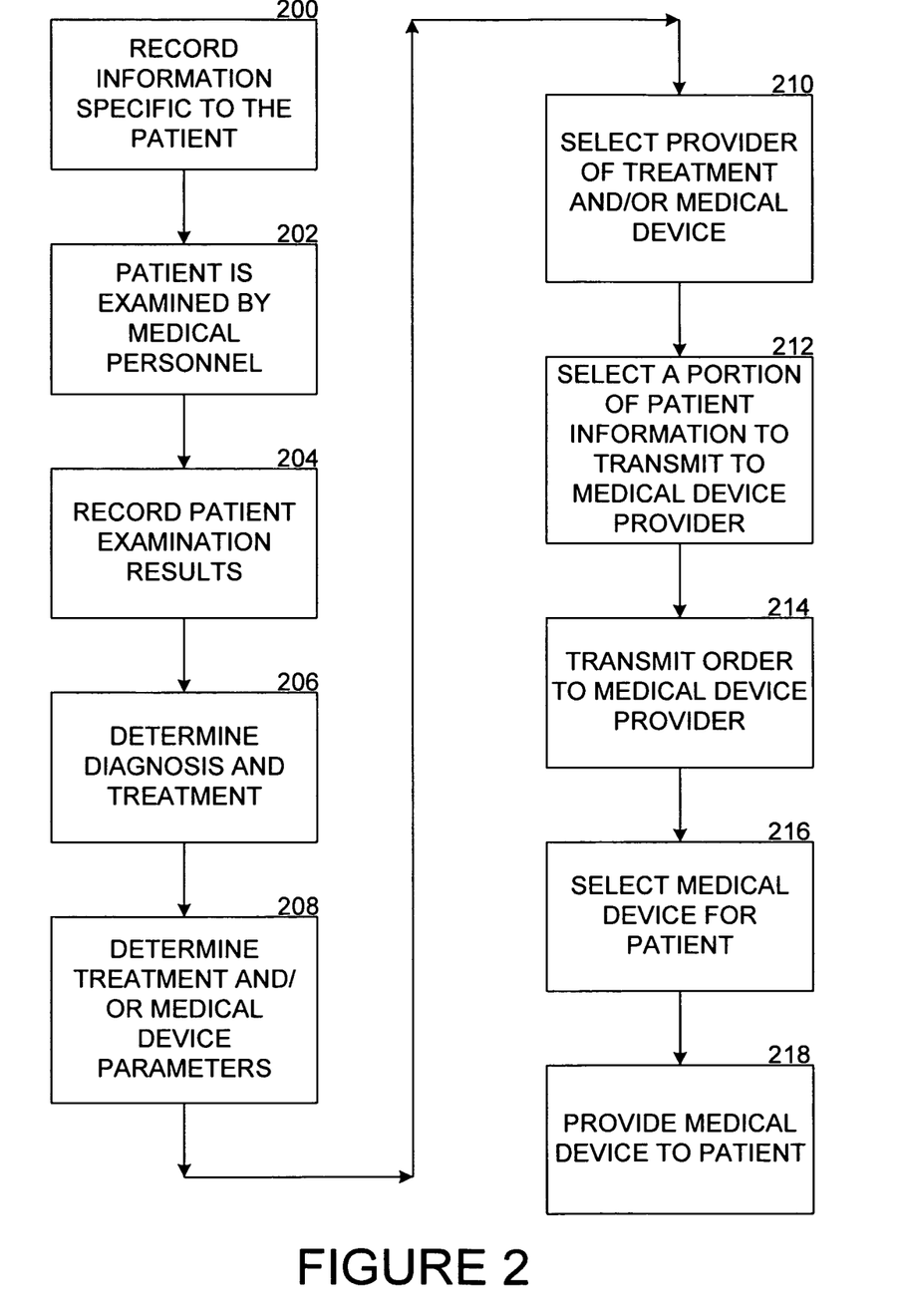
Figure 3:
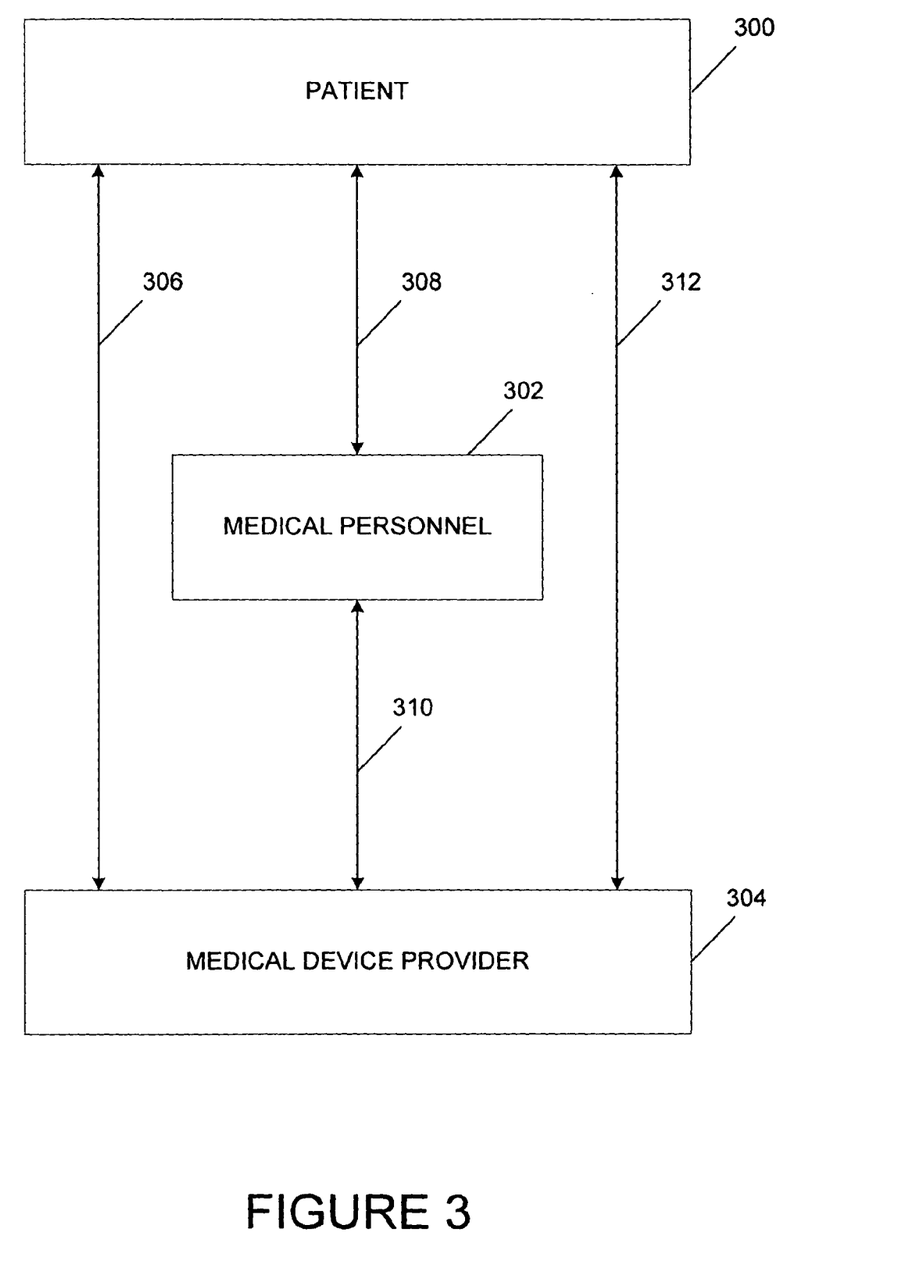

Referring now to FIG. 2, there is shown a block flow chart of a method for providing a medical device to a patient according to exemplary embodiments. Referring also to FIG. 3, there is shown a block chart of the information flow among medical personnel 302, a patient 300, and a provider of a medical device 304 during the process of FIG. 2. In conjunction with FIGS. 1, 2, and 3, the process of exemplary embodiments begins with the recording at step 200 of information specific to a patient 300 at the office of medical personnel 302. Such patient-specific information can include patient history, such as past medical occurrences, issues, and problems. Such information can also include personal information of name, address, date of birth, gender, ancestry, financial information, and allergies. Financial information can include bank account and/or credit account information for subsequent payment for the purchase and delivery of a medical device to the patient 300. This information specific to the patient is recorded by the medical personnel for immediate or eventual storage on the storage device 106 of the computer 102 of the medical personnel or doctor. The patient is also examined by medical personnel at step 202, and the patient's current condition is determined. The results of the patient's examination are recorded on the storage device 108 of the medical personnel's computer 102 at step 204. The patient can be examined with use of equipment that determines patient health conditions electronically and/or automatically. Such equipment, such as a heart monitor or a blood pressure cuff, can automatically record the examination results on the medical personnel's computer 102, thereby providing greater efficiency and accuracy. The patient history and examination information selected to be taken and recorded can be determined based on the medical device to be prescribed for the patient. While FIG. 1 shows the storage of the patient's specific information and examination results on different devices 106 and 108, exemplary embodiments provide that the information can be stored on a single device and/or within the computer 102 itself, such as on a hard drive of the computer 102.

The medical personnel 302 determine, optionally with assistance of the computer 102, and based on the patient-specific information and the patient examination results, an appropriate diagnosis and treatment for the patient 300 at step 206. For example and not limitation, the medical personnel 302 can determine that the patient needs a medical device, such as contact lenses to improve the patient's vision. The medical personnel 302 can further determine the particular treatment and/or medical device parameters needed at step 208 and can select the particular medical device provider 304 to provide the treatment and/or medical device to the patient 300 at step 210. In terms of the medical device being contact lenses, such parameters can include diopter, axis of astigmatism, cylinder power, and lens modality. Selection of the particular medical device provider 304 is performed by the medical personnel 302 based on the needs of the patient, the recorded patient information and examination results, and the knowledge of the medical personnel.

In one embodiment, the selection of the medical device parameters and/or the medical device provider 304 is automatically performed by the medical personnel's computer 102, based on patient information recorded in storage devices 106 and 108, medical device provider information recorded in storage device 107, and parameters provided by the medical personnel 302. The medical device provider information can comprise the treatments and products available by the provider, product information such as product advantages and limitations, and provider contact information. The medical personnel-provided parameters can include product and/or provider information weighted such that particular products and/or providers 304 are preferable in particular situations so that the patient 300 is provided the best product from a preferred provider 304. For example, if a toric contact lens is determined by the medical personnel 302 or the medical personnel's computer 102 to address a patient's astigmatism, this embodiment can select the best provider 304 for toric contact lenses for this patient. Similarly, if the patient's lifestyle lends itself to disposable lenses, the system can determine the best provider or providers for the particular disposable contact lenses needed by the patient.

In an alternate embodiment, the medical personnel 302 (or the computer 102) can determine two or more particular medical device providers 304 who are qualified to provide the medical device to the patient 300, and the medical personnel 302 can present this selection to the patient 300. In this embodiment, the patient 300 can make a selection of a particular medical device provider 304, to provide the device to the patient 300, from among the possible device providers 304 selected by the medical personnel 302 and presented to the patient 300.

Once the particular medical device provider for the patient 300 has been selected, portions of the recorded patient information and portions of the recorded patient examination results are automatically selected by the medical personnel computer 102 at step 212 and transmitted to the computer 104 of the selected medical device provider at step 214. The patient information selected for transmission to the medical device provider 304 is kept to a minimum to limit distribution of confidential and/or private patient information beyond the patient's computer 100 and the medical personnel's computer 102. Accordingly, the medical device provider 304 does not have direct access to the information stored on the storage devices of the medical personnel's computer 102 or on the storage devices (not shown) of the patient's computer 100. The selected patient information can comprise, for example, patient name, address, date of birth, and financial information, such as a credit account for payment purposes.

Along with the selected patient information, the information describing the medical device being ordered is also transmitted to the medical device provider 304 at step 214. Order parameter information can be included in the order information transmitted to the medical device provider 304. Order parameter information can include information regarding future refill information and any medical personnel authorization information. For example, the order information can specify whether and how many refills of the order/prescription can be reordered. This feature can be convenient for the patient, whereby medical device reorders, such as for disposable contact lenses, can be established at the time of ordering the initial lenses and can be established for future order refills at specific intervals or upon request by the patient or the medical personnel.

This information can also include a parameter determining whether the medical personnel are to be contacted for order refill authorization at the time of future refills of the medical device. This feature keeps the medical personnel involved in the subsequent delivery of reorders of the medical device to the patient. For example, for a particular patient and medical device, perhaps it would be advisable for the patient to be reexamined after one year before additional medical devices of the same type and parameter are provided to the patient. In this manner, the medical personnel can request the patient to come in and be examined prior to transmitting a reorder approval to the medical device provider. If the medical personnel 302 decline to authorize the order refill, the medical device provider 304 can so advise the patient 300 directly across the network 118. Alternately, the order parameter information can merely instruct the medical device provider to notify the medical personnel each time a reorder is filled. In yet another embodiment, the medical device, for the initial order and optionally for subsequent device reorders, can be delivered to the medical personnel for personal delivery to and/or fitting to the patient.

At step 216, the medical device provider 304 selects the particular medical device based on the transmitted order information and medical device information available from the storage device/file 110. The medical provider 304 also records the received patient information in a storage device 111. The medical device provider 304 also records in device 111 any reorder information and medical personnel notification requirements as determined from the received order information and order parameters. In this manner, the medical device provider 304 utilizes two limited files or databases on devices 110 and 111 such that the patient information available to the medical device provider 304 is limited.

The medical device provider 304 then provides the medical device to the patient 300 at step 218. The manner of shipment of the medical device to the patient 300 and whether the medical device is delivered to the medical personnel 302 instead of the patient 300 is determined by the order parameter information either received with the order information or already on file for this particular patient 300. The medical device provider 304 also provides notification to at least the medical personnel 302 and optionally also to the patient 300 that the medical device is being or has been shipped, along paths 310 and 312.

Patient financial information can be provided to the medical device provider 304 in the patient information transmitted to the medical device provider 304 at step 214. The medical device provider 304 can efficiently recover its charges, such as by debiting a patient charge account, for the delivery of the medical device. In an alternate embodiment, no patient financial information is transmitted to the medical device provider 304, and the patient 300 or the medical personnel 302 can be billed for the purchase of the medical device. In this embodiment, actual delivery of the medical device to the patient can be delayed until the medical personnel notify the medical device provider 304 that the patient 300 has paid for the device. In this manner, the medical device provider 304 is more assured of payment prior to sending the medical device to the patient 300.

Upon completion of the order, whether for a new order or for a refill of a previous order, the medical device provider 304 transmits order fulfillment information to the medical personnel 302, identifying the device delivered and the patient 300 to whom the device was sent. The medical device provider 304 can also transmit order fulfillment information to the patient 300, thereby notifying the patient 300 that the medical device order has been fulfilled and that the device is being shipped to either the patient 300 or the medical personnel 302. Order information and order fulfillment information can be transmitted across the network 118, for example and not limitation, by means of email messages, telephone voice messages, and/or by file to file transfers.

In another embodiment of the medical device providing system, the patient 300 can access the computer system 104 of the medical device provider 304 for determining the status of a medical device order and/or for submitting a reorder of the medical device. For security and confidentiality purposes, the patient 300 will be required to provide an ID and a password to access the medical device provider's computer system 104. Optionally, the patient 300 can be required to specify a particular device order number to access an existing patient order online. Conveying authorized ID's, passwords, and order numbers to the patient 300 can be effected across the network 118 to the patient's computer 100 from either the medical personnel's computer 102 or the medical device provider's computer 104. In one embodiment, the medical device provider 304 transmits an authorized ID, password, and/or device order number directly to the patient 300 upon receipt of the order from the medical personnel. Alternately, the medical personnel 302 can establish this information and provide it to both the patient 300 and the device provider 304.

Referring now to FIG. 3, there is shown a block chart of information (and optionally products) flowing between a patient 300, medical personnel 302, and a medical device provider 304. Exemplary embodiments begin with the information flow 308 whereby patient-specific information and patient history information is provided by the patient 300 to the medical personnel 302 for recording onto medical personnel storage devices 106. Alternately, information flow 308 can also represent patient examination results, to be recorded onto storage device 108. Information flow 308 can also represent device and/or device provider options presented to the patient 300 by the medical personnel 302 for selection, whereby the selection by the patient 300 flows along the information flow path 308 to the medical personnel. Further, the patient 300 can provide financial and/or payment information along path 308 to the medical personnel 302 for immediate or future payment for any medical device ordered or reordered.

A selected portion of patient information and order information is transmitted from the medical personnel 302 to the medical device provider 304, as represented by the information flow 310. All authorization requests from the device provider 304 to the medical personnel 302 for the fulfillment of a particular order or reorder and for the delivery of the ordered device to the patient flow along information path 310. The resulting authorization or denial flows from the medical personnel 302 to the medical device provider 304 along the same path 310. Similarly, the ordered medical device can be delivered to the medical personnel 302 from the device provider 304. In this embodiment, the patient 300 is notified by the medical personnel 302 along path 308 that the medical device has been received and is ready for pickup and/or fitting.

The information flow 310 can also provide payment information to the medical device provider 304, whether the information comprises patient account information for charging the cost of the device or comprises device cost information sent to the medical personnel 302 for charging to the patient 304 and a resultant payment confirmation from the medical personnel 302.

Alternately, the medical device can be provided directly to the patient 300 from the medical device provider along the path represented by element 306. An information flow between the patient 300 and the medical device provider 304 is provided along path 312 for the patient 300 to access order status, submit reorder requests, and be notified by the medical device provider 304 that the device is being shipped or has been shipped, whether to the patient 300 directly or to the medical personnel 302.

Figure 4:
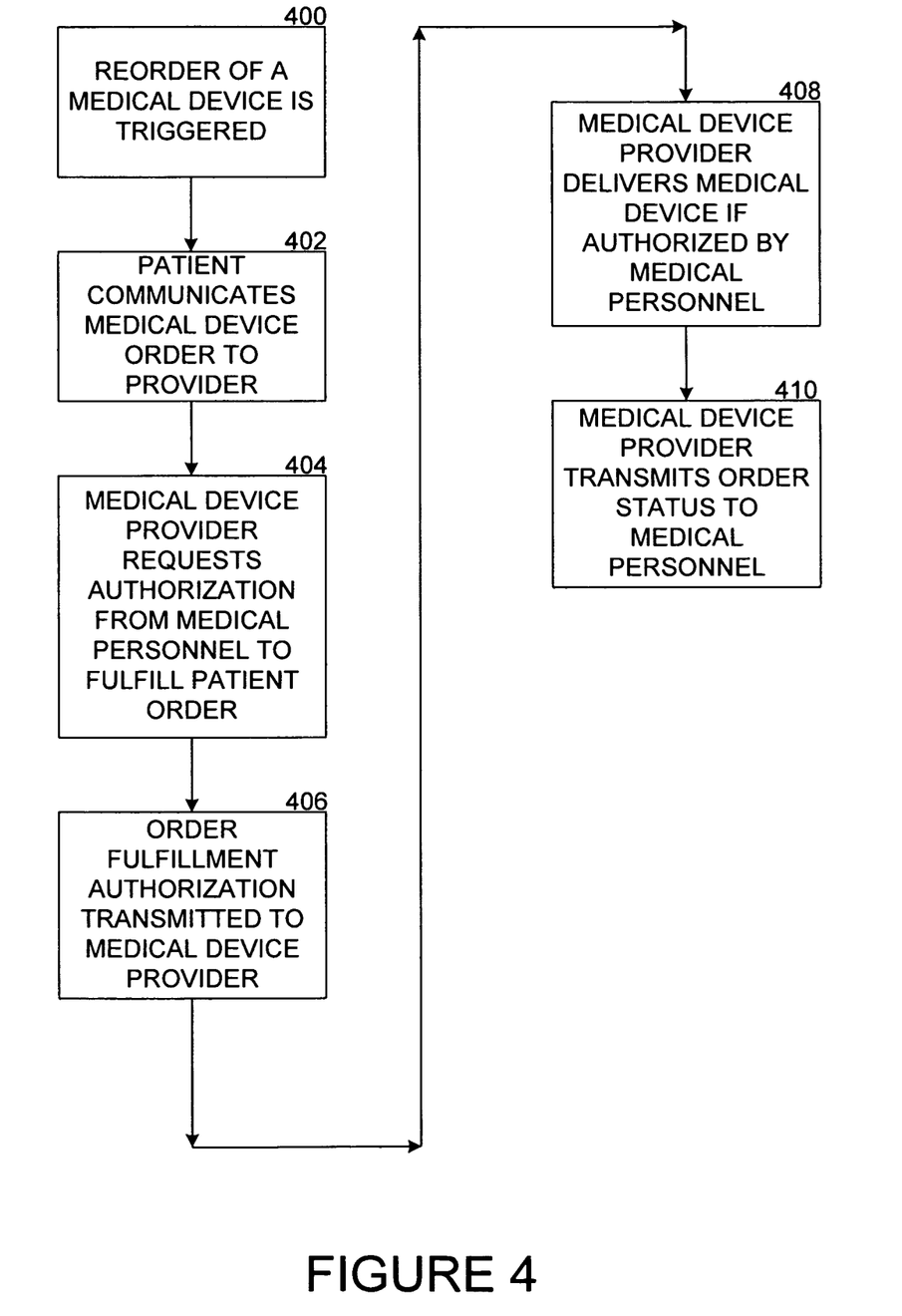

Referring now to FIG. 4, there is shown a block flow chart of an exemplary method for providing a reordered medical device to a patient 300. At step 400, the reorder of a medical device is triggered. This reorder trigger/decision can be on demand by the patient and/or can be regularly scheduled by exemplary embodiments. For example, if the device(s) being reordered are 2-week disposable contact lenses, then the order/reorder system can automatically trigger with the medical device provider 304 a reorder of a 2-week supply of the device at 2-week intervals during the reorder time period authorized by the medical personnel, such as at the initial device order event. If the patient 300 is determining a medical device reorder, the patient 300 communicates the reorder along path 312 to the medical device provider 304 at step 402. The reorder can be automatically submitted into the medical device provider's computer 104 for comparing against patient information stored on storage device 111. If the patient information indicates that prior authorization is required to fulfill the reorder, the medical device provider's computer 104 can transmit a medical device reorder authorization request to the medical personnel's computer 102 at step 404. The medical personnel's computer 102 compares the received device reorder request against the patient information stored on storage devices 106 and/or 108. The patient information stored on the medical personnel's computer 102 can include, for example, the number of reorders that have been authorized by the medical personnel 302 and the number of reorders that have already been requested and fulfilled. This latter information can include the dates of the reorders and the device quantities of each such reorder request fulfilled. If reorders are still available, the number of remaining orders is decremented by one, and an authorization is transmitted to the medical device provider's computer 104 along path 310 at step 406. Alternately, the medical personnel can insert a flag in the patient information stored on devices 106 and/or 108 indicating that the medical personnel are to be notified for each reorder request or for each reorder request after a specified date or specified number of reorders. In this embodiment, the medical personnel's computer 102 outputs a signal to the medical personnel 302 that a device reorder request has been received that requires their attention. The request receipt signal can be in any number of forms, including a printed form, an audible signal, an email message, or a message displayed on the screen of computer 102. According to one exemplary embodiment, a reordered medical device cannot be provided to a patient 300 without authorization from the medical personnel 302.

Upon receipt of authorization from the medical personnel 302, the medical device provider 304 fulfills the order and provides the device to the patient 300, often by placing the order in the mail or with a delivery service at step 408. The system generates and transmits a message to the patient 300 and/or to the medical personnel 302 that the order has been fulfilled at step 410. If the reorder is denied by the medical personnel 302 and/or the medical personnel's computer 102, a message to that effect is transmitted to the medical device provider 304 and, optionally, to the patient 300, also at step 410. In the case of a reorder denial, the medical personnel 302 are notified by the system as above and communicate with the patient to explain the reorder denial and, for example, request the patient come in for an updated examination.

Exemplary embodiments of the described system and method for providing a medical device to a patient 300 address the problem of efficiently, automatically, and reliably providing a medical device to a patient 300 based on the medically-determined needs of the patient 300 while ensuring that the best device provider 304 is selected and that payment is promptly directed to the medical device provider 304. The patient information and the medical device provider information is analyzed to provide the best match among the patient 300, the prescribed device, and the device provider 304 while enabling the medical personnel 302 to remain involved in the transactions of delivering the proper device to the patient 300, both initially and through subsequent reorders. The described system and methods include and implement the technical aspects and considerations of the computer/processor/network-based system and devices described herein in FIG. 1 whereby the unique processing, decision-making, information gathering and transmission, and communications of exemplary embodiments work together to effectively deliver appropriately-diagnosed medical devices from approved providers 304 to the patient 300. Accordingly, exemplary systems and methods provide a tangible and technical effect of selecting and delivering a medically appropriate medical device from an approved provider 304 for the benefit of a patient 300, based on the examination and history of the patient 300.

Although preferred embodiments of the present invention have been shown and described, it will be appreciated by those skilled in the art that changes may be made in these embodiments without departing from the principle and spirit of the invention, the scope of which is defined in the appended claims and their equivalents.

What is claimed is:

1. A computer-based method for providing a medical device to a patient, comprising:
   recording, by medical personnel, information specific to a patient into a medical personnel computer readable storage medium of a medical personnel computer including medical personnel computer-executable instructions for directing processing of the medical personnel computer;
   the medical personnel computer automatically determining medical device parameters and selecting a provider of a medical device for the patient;
   the medical personnel computer automatically selecting a portion of the recorded patient information;
   the medical personnel computer transmitting the selected portion of the recorded patient information to a medical device provider computer readable storage medium of medical device provider computer including medical device provider computer-executable instruction for directing processing of the medical device provider computer of the selected medical device provider;
   the medical personnel computer transmitting medical device order information to the selected medical device provider computer;
   the medical device provider computer automatically selecting the medical device based on the transmitted patient and order information;
   the medical device provider computer transmitting medical device selection information to the medical personnel computer; and
   providing the selected medical device to the patient.

2. The method according to claim 1, wherein the recorded information specific to a patient includes results of an examination of the patient.

3. The method according to claim 1, wherein the information specific to a patient comprises:
   medical history information and;
   current health information.

4. The method according to claim 1, wherein at least part of the recorded information is directed toward prescribing a medical device for the patient.

5. The method according to claim 1, wherein the information specific to a patient is automatically recorded from an electronic file associated with the patient.

6. The method according to claim 1, wherein the information specific to a patient is automatically recorded from measuring equipment.

7. The method according to claim 1, wherein the information specific to the patient to be recorded is automatically determined based on the medical device to be provided.

8. The method according to claim 1, wherein the portion of information to be selected is determined based on the medical device to be provided to the patient.

9. The method according to claim 1, wherein the medical device to be provided is contact lenses.

10. The method according to claim 1, wherein the medical device to be provided is eye glasses.

11. The method according to claim 1, wherein the provider of the medical device is selected by the patient.

12. The method according to claim 1, wherein the patient is examined by medical personnel and wherein the examining medical personnel select the provider of the medical device.

13. The method according to claim 1, wherein providing the selected medical device to the patient includes providing notification that the selected medical device is to be delivered to the patient.

14. The method according to claim 1, wherein providing the selected medical device to the patient includes delivering the selected medical device to the medical personnel.

15. A computer-based system for providing a medical device to a patient, comprising:
   a medical computer recording information specific to a patient and recording results of an examination of the patient;
   a processor on the medical computer selecting a portion of the recorded patient information and a portion of the recorded examination results, wherein at least part of the selected portions are determined based on a medical device to be provided to the patient;
   a communications device transmitting the selected portions of the recorded patient information and the recorded examination results to a provider of the medical device;
   a provider computer receiving the transmitted selected portions of the patient information and the examination results; and a processor on the provider computer selecting the medical device for the patient based on the transmitted patient information and examination results and providing notification that the selected medical device is to be delivered to the patient.

16. The system according to claim 15, wherein the medical computer and the provider computer are separate and distinct computers.

17. The system according to claim 15, wherein the notification is sent to the medical personnel and the patient.

18. A non-transitory computer-readable medium encoded with computer-executable instructions, which, when executed by a computer, provide for the delivery of a medical device to a patient, wherein the instructions are provided for:
recording, by medical personnel, patient information into a medical personnel computer readable storage medium of a medical personnel computer including medical personnel computer-executable instructions for directing processing of the medical personnel computer;
examining the patient for application of a medical device;
recording the results of the patient examination into the medical personnel computer;
the medical personnel computer automatically selecting a portion of the recorded patient information and a portion of the recorded examination results, wherein the portions of information to be selected are determined based on the medical device to be provided to the patient;
the medical personnel computer transmitting the selected portions of the recorded patient information and the recorded examination results to a medical device provider computer readable storage medium of medical device provider computer including medical device provider computer-executable instruction for directing processing of the medical device provider computer;
the medical device provider computer automatically selecting the medical device based on the transmitted patient information and examination results;
the medical device provider computer transmitting information describing the selected medical device to the medical personnel computer; and
the medical device provider computer providing notification that the selected medical device is to be delivered to the patient.

19. A computer-based method for providing a medical device to a patient, comprising:
providing a medical personnel computer to automatically trigger a medical device reorder request to a medical device provider computer readable storage medium of medical device provider computer including medical device provider computer-executable instruction for directing processing of the medical device provider computer;
the medical device provider computer determining whether the reorder request for a medical device has been authorized, by medical personnel, for the patient;
the medical device provider computer transmitting a request for approval of the reorder to the medical personnel;
the medical device provider computer receiving, from the medical personnel computer, a response to the request for approval of the reorder request;
the medical device provider computer selecting the medical device to be delivered based on patient and medical device information and based on the reorder authorization;
the medical device provider computer transmitting information describing the selected medical device to be reordered to the medical personnel computer; and
providing the selected medical device to the patient.

20. A computer-based method for providing a medical device to a patient, comprising:
recording, by medical personnel, information specific to a patient into a medical personnel computer readable storage medium of a medical personnel computer including medical personnel computer-executable instructions for directing processing of the medical personnel computer;
examining the patient for application of a medical device;
recording the results of the patient examination into the medical personnel computer;
the medical personnel computer automatically selecting a portion of the recorded patient information and a portion of the recorded examination results, wherein the portions of information to be selected are determined based on the medical device to be provided to the patient;
the medical personnel computer transmitting the selected portions of the recorded patient information and the recorded examination results to a medical device provider computer readable storage medium of medical device provider computer including medical device provider computer-executable instruction for directing processing of the medical device provider computer;
the medical device provider computer automatically selecting the medical device based on the transmitted patient information and examination results;
the medical device provider computer transmitting information describing the selected medical device to the medical personnel computer; and
providing the selected medical device to the patient.

* * * * *